(12) United States Patent
Hu et al.

(10) Patent No.: US 8,333,808 B2
(45) Date of Patent: Dec. 18, 2012

(54) HAIR DYEING AGENT, HAIR DYEING PRODUCT COMBINATION, AND ITS USE METHOD

(75) Inventors: Liu Hu, Zhejiang (CN); Hongying Lan, Zhejiang (CN); Lian Xue, Zhejiang (CN)

(73) Assignee: Natural Medicine Institute Of Zhejiang Yangshengtang Co., Ltd., Zhejiang (CN)

( * ) Notice: Subject to any disclaimer, the term of this patent is extended or adjusted under 35 U.S.C. 154(b) by 0 days.

(21) Appl. No.: 13/379,952

(22) PCT Filed: Jun. 24, 2010

(86) PCT No.: PCT/CN2010/000938
§ 371 (c)(1),
(2), (4) Date: Feb. 6, 2012

(87) PCT Pub. No.: WO2010/148648
PCT Pub. Date: Dec. 29, 2010

(65) Prior Publication Data
US 2012/0132225 A1     May 31, 2012

(30) Foreign Application Priority Data
Jun. 24, 2009 (CN) .......................... 2009 1 0139489

(51) Int. Cl.
*A61Q 5/10* (2006.01)

(52) U.S. Cl. .............. 8/405; 8/425; 8/435; 8/460; 8/623
(58) Field of Classification Search .............. 8/405, 425, 8/435, 460, 623
See application file for complete search history.

(56) References Cited

FOREIGN PATENT DOCUMENTS

| | | |
|---|---|---|
| CN | 1394590 | 2/2003 |
| CN | 1418612 | 5/2003 |
| CN | 1686075 | 10/2005 |

OTHER PUBLICATIONS

English abstract of the JP Patent No. 53052633 A dated May 13, 1978.*
International Search Report for PCT/CN2010/000938, 2009.

\* cited by examiner

*Primary Examiner* — Eisa Elhilo
(74) *Attorney, Agent, or Firm* — Pillsbury Winthrop Shaw Pittman, LLP

(57) ABSTRACT

A hair dyeing agent, a combination of the hair dyeing agent and a softener for dyeing hair and the method of using the combination are disclosed. The hair dyeing agent comprises a dye active, a mordant active, a stabilizer, water, and a carrier and/or an excipient. The dye active is selected from gallic acids, salts and esters thereof and their combinations. The mordant active is a ferrous salt selected from ferrous sulfate, ferrous chloride, ferrous nitrate, ferrous gluconate, ferrous lactate and ferrous fumarate.

16 Claims, No Drawings

HAIR DYEING AGENT, HAIR DYEING PRODUCT COMBINATION, AND ITS USE METHOD

CROSS REFERENCE TO RELATED APPLICATIONS

This application is the U.S. National Stage of PCT/CN2010/000938, filed Jun. 24, 2010, which in turn claims priority to Chinese Patent Application No. 2009101139489.X, filed Jun. 24, 2009, the entire contents of all applications are incorporated herein by reference in their entireties.

TECHNICAL FIELD

The present invention belongs to the technical field of cosmetic industry, and specifically relates to a hair dyeing agent for a hair dyeing product combination, a hair dyeing product combination comprising the hair dyeing agent, and a use method thereof. The present invention particularly relates to a non-oxidative permanent natural hair dyeing agent, especially a two-part natural hair blackening product combination.

BACKGROUND ART

As the living standard improves, hair dyeing has become one method for people to pursue vogue and beauty. According to the used materials, the hair dyeing agents sold presently on the market may be classified into three types: the first one is chemically synthesized hair dyeing agent that occupies most of the market share, wherein harmful substances such as thioglycolic acid, p-phenylenediamine and hydrogen peroxide are added; the second one is chemically synthesized hair dyeing agent with "natural" concept that occupies a little of the market share, wherein some plant ingredients are added, but p-phenylenediamine and the like are also included therein; and the third one is natural dyeing agent that occupies a thimbleful of the market share. The foregoing two types of hair dyeing agents can be used in a convenient and quick way, but they are more allergenic and potentially carcinogenic, and damage the hair. Although the natural hair dyeing agents sold presently on the market are safe and not-stimulating, they are generally three-part, for example, "Sanjing" sorghum red natural hair dyeing agent, "Yipin" natural hair dyeing agent, "Laorentou" galla rhois gallnut natural dyeing agent and the like as manufactured in China, and all of them require many times of application and washing. And, most of them even require a relatively high temperature such as 40° C. or above so as to achieve colorizing, which leads to a quite complicated operation and a long hair dyeing time. Meanwhile, due to poor stability, these natural hair dyeing agents must be used up once they are unsealed, which results in unnecessary resource waste and aggravates economic burden of the consumers.

Three-part natural hair dyeing agents occurred presently on the market (for example, the Chinese patent application No. 200910009172.4 as filed by the applicant on Feb. 20, 2009, which is incorporated herein in its entirety by reference) generally comprise three independent compositions, i.e., usually said softener part, mordant part and dye part. The softener part mainly acts to soften the hair by opening disulfide linkage in the hair using a disulfide linkage reducing agent such as a cysteine substance. The mordant part mainly acts to enable the dye active to dye onto the hair via mordant active therein. The dye part comprises dye active, i.e., usually said coloring agent. Due to the incompatibility among the actives in the various parts and the actual requirement in hair dyeing operation, it is difficult to mix the above three parts into a homogenous composition, which thereby leads to complexity in manufacture and dyeing operation.

Due to the above problems, the existing natural hair dyeing agents have a poor acceptance in consumers. Thus, there needs to develop a hair dyeing agent or a hair dyeing product combination that is safe, nontoxic, not-stimulating, stable, simple to operate and easy to dye.

CONTENTS OF THE INVENTION

The object of the present invention is to provide a non-oxidative permanent two-part natural hair dyeing agent, particularly hair blackening agent, which is not only safe, not-stimulating, and good in hair dyeing chroma and fastness, but also superior to the existing products in terms of product stability and use convenience. The present inventors surprisingly found that, by using gallic acid naturally existed in tannins as a dye active and ferrous salt as a mordant active, the existing dye part and mordant part can be mixed into a homogenous composition, which not only has good safety, but also could confer good dyeing chroma and fastness on the hair by means of synchronous mordant dyeing. In this case, the existing products which are limited to a three-part mode can be changed into those in a two-part mode, so that the operation steps can be simplified and the operation time can be shortened to a very great extent. The present inventors further found that the formulation with good stability can be obtained by adjusting the pH value to be within a suitable range. To achieve the above object, in the technical solution of the present invention, by using natural actives as materials, two parts are formulated for combination use.

SUMMARY OF THE INVENTION

The first aspect is to provide a hair dyeing agent for hair dyeing product combination, which comprises an effective amount of a dye active, an effective amount of a mordant active, a stabilizer, water, and optionally a carrier and/or an excipient.

The hair dyeing agent as recited in any item of the first aspect, wherein the dye active is one or more selected from gallic acid and salts or esters thereof. In one embodiment, the dye active is gallic acid.

The hair dyeing agent as recited in any item of the first aspect, wherein the amount of the dye active, based on the total weight of the hair dyeing agent, is 0.5~10% by weight, preferably 2~8% by weight.

The hair dyeing agent as recited in any item of the first aspect, wherein the mordant active is a ferrous salt. In one embodiment, the ferrous salt is selected from ferrous sulfate, ferrous chloride, ferrous nitrate, ferrous gluconate, ferrous lactate, and ferrous fumarate.

The hair dyeing agent as recited in any item of the first aspect, wherein the amount of the mordant active, based on the total weight of the hair dyeing agent, is 1~15% by weight, preferably 2~10% by weight.

The hair dyeing agent as recited in any item of the first aspect, wherein the stabilizer is selected from sulfites, bisulfites, thiosulfates, ascorbic acid or salts thereof, cysteine or derivatives and salts thereof.

The hair dyeing agent as recited in any item of the first aspect, wherein the amount of the stabilizer, based on the total weight of the hair dyeing agent, is 0.1~8% by weight, preferably 0.2~5% by weight, preferably 0.5~2.5% by weight.

The hair dyeing agent as recited in any item of the first aspect, which further comprises a penetration enhancer and/or a thickener.

The hair dyeing agent as recited in any item of the first aspect, wherein the penetration enhancer includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer may be one or more selected from oleyl alcohol, dodecyl sulfate or other anionic surfactant, fatty alcohol ether or other nonionic surfactant, cocamido propyl betaine or other amphoteric surfactant. The hair dyeing agent as recited in any item of the first aspect, wherein the penetration enhancer may be used alone or in a mixture of any of the above penetration enhancers.

The hair dyeing agent as recited in any item of the first aspect, wherein the thickener is one or more selected from fatty alcohols (for example, cetyl alcohol, stearyl alcohol) or high molecular polymers such as carbomer, hydroxyethyl cellulose and the like.

The hair dyeing agent as recited in any item of the first aspect, which has a pH value of 1.5~8, preferably 2~7, more preferably 2.5~4, for example, a pH value of 3.

The hair dyeing agent as recited in any item of the first aspect, which is in the form of emulsion, paste or gel. That is, it is usually emulsion, cream, ointment or gel.

The second aspect is to provide a hair dyeing product combination, which comprises two parts, i.e., a softener part and the hair dyeing agent part as recited in any item of the first aspect.

The hair dyeing product combination as recited in any item of the second aspect, wherein the softener comprises an effective amount of a disulfide linkage reducing agent, an alkalizer and water.

The hair dyeing product combination as recited in any item of the second aspect, wherein the disulfide linkage reducing agent in the softener is one or more selected from mercapto compounds such as cysteine or derivatives and salts thereof, urea, thiosulfates, sulfites, and bisulfites.

The hair dyeing product combination as recited in any item of the second aspect, wherein the amount of the disulfide linkage reducing agent in the softener, based on the total weight of the softener, is 2~30% by weight, preferably 4~25% by weight.

The hair dyeing product combination as recited in any item of the second aspect, wherein the alkalizer in the softener is one or more selected from ornithine, arginine, lysine, ammonia, ethanolamines (for example, monoethanolamine, diethanolamine, triethanolamine), alkyl alcohol amide, hydroxides, or carbonate-containing compositions.

The hair dyeing product combination as recited in any item of the second aspect, wherein the amount of the alkanizer in the softener, based on the total weight of the softener, is 0.5~30% by weight, preferably 5~25% by weight.

The hair dyeing product combination as recited in any item of the second aspect, wherein the softener further comprises a penetration enhancer and/or a thickener.

The hair dyeing product combination as recited in any item of the second aspect, wherein the penetration enhancer includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer may be oleyl alcohol, dodecyl sulfate or other anionic surfactant, fatty alcohol ether or other nonionic surfactant, cocamido propyl betaine or other amphoteric surfactant, and the penetration enhancer may be used alone or in a mixture of any of the above penetration enhancers.

The hair dyeing product combination as recited in any item of the second aspect, wherein the thickener in the softener is one or more selected from fatty alcohols (for example, cetyl alcohol, stearyl alcohol) or high molecular polymers including carbomer, hydroxyethyl cellulose and the like.

The hair dyeing product combination as recited in any item of the second aspect, wherein the softener has a pH value of 8~11, preferably 8.5~10.5, more preferably 9~10, for example, a pH value of 9.5.

The hair dyeing product combination as recited in any item of the second aspect, wherein the softener is in the form of emulsion, paste or gel. That is, the softener is usually emulsion, cream, ointment or gel.

The hair dyeing product combination as recited in any item of the second aspect, which further comprises information instructing the consumer to use the hair dyeing product combination.

The hair dyeing product combination as recited in any item of the second aspect, wherein the information at least comprises: a) applying the softener onto the hair; and b) applying the hair dyeing agent as recited in any item of the first aspect onto the hair. In one embodiment, the above a) further comprises keeping at a suitable temperature for a suitable period of time after applying the softener onto the hair. In one embodiment, the above a) further comprises keeping at a temperature of 15~60° C. (preferably 20~40° C.) for 5~60 minutes (preferably 20~40 minutes) after applying the softener onto the hair. In one embodiment, the above b) further comprises keeping at a suitable temperature for a suitable period of time after applying the hair dyeing agent onto the hair. In one embodiment, the above b) further comprises keeping at a temperature of 15~60° C. (preferably 20~40° C.) for 2~20 minutes (preferably 3~7 minutes) after applying the hair dyeing agent onto the hair.

The hair dyeing product combination as recited in any item of the second aspect, wherein the information further comprises one or more of the following:

uniformly applying the softener onto the hair repeatedly;

uniformly applying the hair dyeing agent onto the hair repeatedly;

washing the hair with water after the completion of treating the hair with the softener; and washing the hair with water after the completion of treating the hair with the hair dyeing agent.

The hair dyeing product combination as recited in any item of the second aspect, wherein the information at least comprises the following: i) uniformly mixing the softener and the hair dyeing agent as recited in any item of the first aspect in a weight ratio of 1:0.1 to 1:10 (preferably 1:0.2 to 1:8, more preferably 1:0.5 to 1:5, further preferably 1:0.5 to 1:2.5); and ii) applying the mixture obtained in the i) onto the hair. In one embodiment, the above ii) further comprises keeping at a suitable temperature for a suitable period of time after applying the mixture onto the hair. In one embodiment, the above ii) further comprises keeping at a temperature of 15~60° C. (preferably 20~50° C.) for 5~120 minutes (preferably 10~100 minutes, more preferably 20~80 minutes, further preferably 20~60 minutes) after applying the mixture onto the hair.

The hair dyeing product combination as recited in any item of the second aspect, wherein the information further comprises one or more of the following: uniformly mixing the softener and the hair dyeing agent as recited in any item of the first aspect in a weight ratio of 1:0.1 to 1:10 (preferably 1:0.2 to 1:8, more preferably 1:0.5 to 1:5, further preferably 1:0.5 to 1:2.5); uniformly applying the resulting mixture onto the hair repeatedly; and washing the hair with water after the completion of treating the hair with the mixture.

The third aspect of the present invention is to provide a method of using the hair dyeing product combination as recited in any item of the second aspect, which comprises the steps of:

a) applying the softener onto the hair; and b) applying the hair dyeing agent as recited in any item of the first aspect onto the hair.

The method as recited in any item of the third aspect, wherein step a) further comprises keeping at a suitable temperature for a suitable period of time after applying the softener onto the hair. In one embodiment, the step a) further comprises keeping at a temperature of 15~60° C. (preferably 20~40° C.) for 10~60 minutes (preferably 20~40 minutes) after applying the softener onto the hair.

The method as recited in any item of the third aspect, wherein step b) further comprises keeping at a suitable temperature for a suitable period of time after applying the hair dyeing agent onto the hair. In one embodiment, the step b) further comprises keeping at a temperature of 15~60° C. (preferably 20~40° C.) for 2~20 minutes (preferably 3~7 minutes) after applying the hair dyeing agent onto the hair.

The method as recited in any item of the third aspect, further comprises one or more of the following steps:

uniformly applying the softener onto the hair repeatedly;

uniformly applying the hair dyeing agent onto the hair repeatedly;

washing the hair with water after the completion of treating the hair with the softener; and washing the hair with water after the completion of treating the hair with the hair dyeing agent.

The fourth aspect of the present invention is to provide a method of using the hair dyeing product combination as recited in any item of the second aspect, which comprises the steps of:

i) uniformly mixing the softener and the hair dyeing agent as recited in any item of the first aspect in a weight ratio of 1:0.1 to 1:10 (preferably 1:0.2 to 1:8, more preferably 1:0.5 to 1:5, further preferably 1:0.5 to 1:2.5); and ii) applying the mixture obtained in step i) onto the hair.

The method as recited in any item of the fourth aspect, wherein the step ii) further comprises keeping at a suitable temperature for a suitable period of time after applying the mixture onto the hair. In one embodiment, the step ii) further comprises keeping at a temperature of 15~60° C. (preferably 20~50° C.) for 5~120 minutes (preferably 10~100 minutes, more preferably 20~80 minutes, further preferably 20~60 minutes) after applying the mixture onto the hair.

The method as recited in any item of the fourth aspect, which further comprises one or more of the following steps:

uniformly mixing the softener and the hair dyeing agent as recited in any item of the first aspect in a weight ratio of 1:0.1 to 1:10 (preferably 1:0.2 to 1:8, more preferably 1:0.5 to 1:5, further preferably 1:0.5 to 1:2.5);

uniformly applying the resulting mixture onto the hair repeatedly; and washing the hair with water after the completion of treating the hair with the mixture.

The fifth aspect of the present invention is to provide a softener for use in the hair dyeing product combination as recited in any item of the second aspect.

The softener as recited in the fifth aspect, which has the features of the softener in the hair dyeing product combination as recited in any item of the second aspect.

In one example of the present invention, the object of hair dyeing is achieved according to the following principles: the use of acetylcysteine as a disulfide linkage reducing agent (also called "penetrant") to slightly opens the hair squama; then, the mordant active ferrous ion and the natural dye active gallic acid in the hair dyeing agent simultaneously enter the squama, wherein ferrous ion is oxidized by air into ferric ion and complexed with the natural dye active gallic acid to form a black pigment macromolecule ferric gallate, thereby developing a color. Thus, according to the present invention, the existing mordant and dyeing agent are mixed together to form a new uniform hair dyeing agent, thereby achieving 2 in 1 product, and combining the existing two dyeing steps (i.e., mordanting step and dyeing step) into one dyeing step, and/or combining the step of softening the hair squama and the existing two dyeing steps (i.e., mordanting step and dyeing step) into one dyeing step, so that the dyeing operation is greatly simplified.

The features as described in any aspect of the present invention or any item of the any aspect are similarly applicable to any other aspect or any item of the any other aspect. In the present invention, for example, when the expression "any item of the first aspect" is mentioned, the term "any item" refers to any sub-aspect of the first aspect; when being mentioned in a similar manner in other aspect, it also has the same meaning.

DETAILED DESCRIPTION OF THE PRESENT INVENTION

All reference documents as cited in the present invention are incorporated herein in their entireties by reference. Moreover, if the meanings as expressed by these reference documents are inconsistent with those as described in the present invention, the meanings as described in the present invention are adopted. In addition, various terms and phrases used in the present invention have the general meanings as well known by a person skilled in the art. Even so, the present invention still hopes to make more detailed description and explanation about these terms and phrases. If the meanings of the terms and phrases as described in the present invention are inconsistent with those as well known, the meanings as described in the present invention are adopted.

The object of the present invention is to provide a non-oxidative permanent natural hair dyeing product, particularly hair blackening product, which is not only safe, not-stimulating, and good in hair dyeing chroma and fastness, but also excellent in product stability and use convenience. The present inventors found that bivalent iron salt (i.e., ferrous salt) as a mordant active and gallic acid naturally existed in tannins as a dye active could be combined to obtain a product, which is not only safe, stable, and capable of accomplishing mordanting and dyeing in one step, but also has good dyeing chroma and fastness on the hair by the formation of a ferric complex in the hair.

Gallic acid is a monomer of hydrolysable tannins, which naturally exists in tannins, and is represented by the following structural formula:

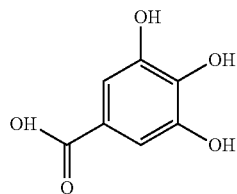

It has a molecular weight of 170.12, and is used as astringent and hemostatic in medicine. Gallic acid appears as a white or light-yellow needle crystal powder. Due to the presence of multiple o-phenolic hydroxyl moieties in the molecule, gallic acid can serve as a polyhydroxy ligand and complex with ferric ion to form a black stable and dense chelate—ferric gallate. According to the present invention, an ester compound of gallic acid can also be used. The ester compound of gallic acid is a compound having ester structure formed by carboxyl group of gallic acid.

In general, the outer layer of hair is covered with hair squama constituted by multi-layer keratin, so gallic acid and metal ion have a poor penetration thereto. In one example of the present invention, acetylcysteine is used as a disulfide linkage reducing agent (also called "penetrant") to reduce —S—S— of keratin in hair cuticle into —SH, thereby softening the hair, relaxing the tension, and opening the hair squama to a certain extent, so that ferrous ion penetrates into cortical layer and medullary layer inside the hair, and is oxidized into ferric ion by the aid of air, thus complex with the gallic acid inside the hair to form a black dye macromolecule:

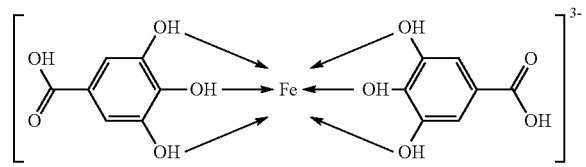

which makes the hair develop a black color, thereafter, the hair squama is closed, and a permanent hair dyeing is formed.

The hair dyeing agent as recited in the first aspect and the softener in the hair dyeing product combination as recited in the second aspect comprise water, and the amount of water may be, for example, a suitable amount as added during the formulation. The addition of a suitable amount of water can enable the principal components in the mordant to attain an expected and/or predetermined concentration. In addition, the hair dyeing agent and the softener in the present invention may do not comprise water, although this is not optimal, the present invention can be similarly carried out.

In the hair dyeing agent as recited in any item of the first aspect, the ferrous salt includes, but not limited to, ferrous sulfate, ferrous chloride, ferrous nitrate, ferrous gluconate, ferrous lactate, ferrous fumarate and the like. In one embodiment, the ferrous salt is selected from ferrous sulfate and ferrous chloride. In one embodiment, the ferrous salt is ferrous sulfate. In the hair dyeing agent of the present invention, the ferrous salt may be used alone or in a mixture of any of the above ferrous salts. In the hair dyeing agent as recited in any item of the first aspect, the amount of the ferrous salt, based on the total weight of the hair dyeing agent, is 1~15% by weight. In one embodiment, the amount of the ferrous salt, based on the total weight of the hair dyeing agent, is 2~10% by weight.

In the hair dyeing agent as recited in any item of the first aspect, the dye active includes, but not limited to, one or more selected from gallic acid and salts or esters thereof. The esters of gallic acid may be, for example, methyl, ethyl, and propyl esters of gallic acid. In one embodiment, the dye active is gallic acid. In one embodiment, the amount of the dye active, based on the total weight of the hair dyeing agent, is 0.5~10% by weight, preferably 2~8% by weight.

In the hair dyeing agent as recited in any item of the first aspect, the stabilizer (also called antioxidant) includes, but not limited to, ascorbic acid or salts thereof, cysteine or derivatives and salts thereof, for example, sulfites, bisulfites, ascorbic acid, sodium ascorbate, cysteine and its salts or derivatives (for example, cysteine hydrochloride, N-acetylcysteine), reduced glutathione and the like. In one embodiment, the stabilizer is selected from cysteine or derivatives and salts thereof. In one embodiment, the stabilizer is selected from D-cysteine, L-cysteine, DL-cysteine, N-acetylcysteine, and salts thereof. In one embodiment, the stabilizer is selected from cysteine hydrochloride. According to the hair dyeing agent of the present invention, wherein the stabilizer may be used alone or in a mixture of any of the above stabilizers. In one embodiment, the weight percent of the stabilizer in the hair dyeing agent can be determined by a person skilled in the art according to the teaching of the present invention in combination with the prior art. According to the hair dyeing agent as recited in any item of the first aspect, wherein the amount of the stabilizer, based on the total weight of the hair dyeing agent, is 0.1~8% by weight, preferably 0.2-5% by weight, more preferably 0.5~2.5% by weight.

The hair dyeing agent as recited in any item of the first aspect may further comprise a penetration enhancer. The penetration enhancer includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer may be one or more selected from oleyl alcohol, dodecyl sulfate, dodecyl sulfonate or other anionic surfactant, fatty alcohol ether or other nonionic surfactant, cocamido propyl betaine or other amphoteric surfactant. In one embodiment, the penetration enhancer may be one or more selected from oleyl alcohol, dodecyl sulfate or other anionic surfactant, fatty alcohol ether or other nonionic surfactant, cocamido propyl betaine or other amphoteric surfactant. According to the hair dyeing agent of the present invention, the penetration enhancer may be used alone or in a mixture of any of the above penetration enhancers. In one embodiment, the amount of the penetration enhancer, based on the total weight of the hair dyeing agent, is 1~30% by weight. In one embodiment, the amount of the penetration enhancer, based on the total weight of the hair dyeing agent, is 2~20% by weight.

The hair dyeing agent as recited in any item of the first aspect may further comprise a thickener (i.e., a viscosity adjuster useful for adjusting the state of fluid (e.g., liquid, semi-solid). In one embodiment, the thickener includes, but not limited to, one or more selected from fatty alcohols or high molecular polymers including carbomer, hydroxyethyl cellulose, hydroxypropylmethyl cellulose and the like. In one embodiment, the weight percent of the thickener in the hair dyeing agent can be determined by a person skilled in the art according to the teaching of the present invention in combination with the prior art. Preferably, in one embodiment, the amount of the thickener, based on the total weight of the hair dyeing agent, is 1~15% by weight. In one embodiment, the amount of the thickener, based on the total weight of the hair dyeing agent, is 2~10% by weight.

The hair dyeing agent as recited in any item of the first aspect may further comprise a preservative. In one embodiment, the preservative includes, but not limited to, nipagin esters, for example, methylparaben, ethylparaben, propylparaben and butylparaben. The preservative may be used alone or in a mixture of any of the above preservatives, for example, a mixture of methylparaben and propylparaben in any proportion. In one embodiment, the weight percent of the preservative in the hair dyeing agent can be determined by a person skilled in the art according to the teaching of the present invention in combination with the prior art. Preferably, in one embodiment, the amount of the preservative, based on the total weight of the hair dyeing agent, is 0.1~1.5% by weight. In one embodiment, the amount of the preservative, based on the total weight of the hair dyeing agent, is 0.2~0.8% by weight.

The second aspect of the present invention is to provide a hair dyeing product combination, which comprises two parts, i.e., a softener (the first part) and the hair dyeing agent (the second part) as recited in any item of the first aspect. According to the present invention, the two parts are separate physically, until are applied in a certain order or after being mixed when used for hair dyeing. Thus, in a sense, the hair dyeing product combination of the present invention may be a multi-part hair dyeing product combination.

In the hair dyeing product combination as recited in any item of the second aspect, the softener comprises an effective amount of a disulfide linkage reducing agent, an alkalizer and water. The amount of water may be, for example, a suitable amount as added during the formulation. The addition of a suitable amount of water can enable the principal components in the softener to attain a predetermined concentration. In addition, although the softener part in the present invention may do not comprise water, for the convenience of use, the preferred embodiment in the present invention includes the provision of a softener part that has already been blended with water, for example, a softener for immediate use without any post-treatment. Alternatively, the present invention may provide a concentrated softener part which needs to be suitably diluted just before use.

In one embodiment, the disulfide linkage reducing agent in the softener part includes, but not limited to, one or more selected from mercapto compounds such as cysteine or derivatives and salts thereof, urea, thiosulfates, sulfites, and bisulfites. In one embodiment, the disulfide linkage reducing agent in the softener part is selected from acetylcysteine or salts thereof, cysteine or salts thereof, reduced glutathione, urea, sulfites, and bisulfites. In one embodiment, the amount of the disulfide linkage reducing agent in the softener part, based on the total weight of the softener part, is 2~30% by weight. In one embodiment, the amount of the disulfide linkage reducing agent in the softener part, based on the total weight of the softener part, is 4~25% by weight.

In one embodiment, the alkalizer in the softener part is one or more selected from the following alkalizers: ornithine, arginine, lysine, ammonia, ethanolamines (for example, monoethanolamine, diethanolamine, triethanolamine), alkyl alcohol amide, hydroxides such as sodium hydroxide, or compositions containing carbonate such as sodium carbonate. The amount of the alkalizer in the softener part, based on the total weight of the softener part, is 0.5~30% by weight. In one embodiment, the amount of the alkalizer in the softener part, based on the total weight of the softener part, is 5~25% by weight.

The hair dyeing product combination as recited in any item of the second aspect, wherein the softener part further comprises a penetration enhancer. In one embodiment, the penetration enhancer includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer in the softener part may be one or more selected from oleyl alcohol, dodecyl sulfate, dodecyl sulfonate or other anionic surfactant, fatty alcohol ether or other nonionic surfactant, cocamido propyl betaine or other amphoteric surfactant. In one embodiment, the penetration enhancer in the softener part may be one or more selected from oleyl alcohol, dodecyl sulfate or other anionic surfactant, fatty alcohol ether or other nonionic surfactant, cocamido propyl betaine or other amphoteric surfactant. According to the hair dyeing product combination, wherein the penetration enhancer in the softener part may be used alone or in a mixture of any of the above penetration enhancers. In one embodiment, the amount of the penetration enhancer in the softener part, based on the total weight of the softener part, is 1~10% by weight. In one embodiment, the amount of the penetration enhancer in the softener part, based on the total weight of the softener part, is 2~8% by weight.

In the hair dyeing product combination as recited in any item of the second aspect, the softener part further comprises a thickener (i.e., a viscosity adjuster useful for adjusting the state of fluid (e.g., liquid, semi-solid). In one embodiment, the thickener in the softener part includes, but not limited to, one or more selected from fatty alcohols or high molecular polymers including carbomer, hydroxyethyl cellulose and the like. In one embodiment, the weight percent of the thickener in the softener part, relative to the softener part of the hair dyeing product combination, can be determined by a person skilled in the art according to the teaching of the present invention in combination with the prior art. Preferably, in one embodiment, the amount of the thickener in the softener part, based on the total weight of the softener part, is 0.1~2% by weight. In one embodiment, the amount of the thickener in the softener part, based on the total weight of the softener part, is 0.2~1% by weight.

The various terms used in the present invention have their general meanings in the art. Moreover, in particular, unless otherwise indicated, the following terms used in the present invention have the meanings as defined herein.

As used herein, the term "hair" generally refers to the hair of animals (for example, mammals such as pets and human, particularly human). Particularly, said term may refer to the hair on the head of animals, more particularly the hair on the head of human.

As used herein, the terms "carrier" and "excipient" refer to their general meanings in the art, for example, preservatives and aromatics.

As used herein, the term "hair dyeing product combination" generally refers to a product for colorizing the hair of animals (for example, mammals such as pets and human, particularly human). As to the present invention, since the dye (ferric gallate) is black, the term "hair dyeing product combination" in the present invention may also be called "hair blackening product combination".

As used herein, the term "mordant active" generally refers to an active which is used to enable the "dye active" to dye on an article (for example, textile and hair) to be dyed via a certain medium, to achieve the purpose of dyeing. In the hair dyeing product combination as recited in the second aspect, the two parts, i.e., a softener part and the hair dyeing agent part as recited in the first aspect, sometimes may be respectively called the first part and the second part. The first part and second part are only used to distinguish the two parts, but do not indicate any relationship between them in terms of position, time, size, magnitude and importance. Nevertheless, the softener that is called the first part can take the action of softening in the course of hair dyeing, while the hair dyeing agent that is called the second part can take the action of mordanting and dyeing simultaneously in the course of hair dyeing.

As used herein, the term "ferrous salt" generally refers to salts formed with ferrous ion (e.g., divalent iron ion). Exemplary ferrous salts in the present invention include ferrous sulfate, ferrous chloride, and ferrous nitrate. As is known by a person skilled in the art, the ferrous salts may be extended to ferrous salts formed by in-situ chemical conversion of ferrous compounds, i.e., the ferrous salts in the present invention may be extended to the ferrous compounds, for example, ferrous oxide can be in-situ converted by HCl to form ferrous chloride, i.e., a ferrous salt, so ferrous oxide can also serve as the ferrous salt in the present invention.

As used herein, the term "effective amount" generally refers to the amount of the substance in discussion, for example, the amount of ferrous salt in the hair dyeing agent, and said amount, under general application conditions, usually may result in a basically satisfactory or expected hair dyeing effect.

As used herein, the term "stabilizer" or "antioxidant" generally refers to a substance which is used to prevent an easily oxidized substance from oxidation. For example, the "stabilizer" or "antioxidant" used in the hair dyeing agent of the present invention can prevent the ferrous salt therein from oxidation, and can also enable the dye active such as gallic acid therein to be stable physically and/or chemically.

As used herein, the term "penetration enhancer" generally refers to a substance useful for enhancing the penetration of other substances. For example, the penetration enhancer used in the hair dyeing agent of the present invention can accelerate the entry of ferrous salt into the inside of the hair.

As used herein, the term "thickener" generally refers to a substance useful for adjusting the viscous state of a fluid (for example, liquid, semi-solid), which generally takes the action of increasing the viscosity of the fluid, and may also be called a viscosity adjuster.

The two parts, i.e., the softening agent and the hair dyeing agent, in the present invention may be in the form of emulsion, paste or gel. According to the present invention, the two parts can be in other form certainly, for example, in the form of solution or suspension.

As used herein, the term "softening agent" generally refers to a composition capable of softening keratin in hair cuticle. In the present invention, compositions capable of softening and expanding hair, including disulfide linkage reducing agent and alkalizer, are called "softening agent".

As used herein, the term "dye active" generally refers to an active capable of colorizing fibers, hair and other materials, which differs from the adjuvant used in the present invention to achieve a better effect. In the hair dyeing agent of the present invention, the dye active (for example, gallic acid) per se does not yet form a black complex with the mordant active (for example ferrous sulfate). After entering the hair, the two actives are subjected to hair dyeing treatment, and simultaneously to air oxidation, and thereby form a black complex, which enables the hair to be dyed. The term "dye active" used herein especially refers to gallic acid and esters thereof and the like.

As used herein, the term "disulfide linkage reducing agent" generally refers to a reducing agent, for example, acetylcysteine or derivatives thereof used in the present invention, which is capable of reducing disulfide linkage (—S—S—) in hair into —SH, thereby softening the hair, relaxing the tension, and is favorable for the penetration of the active into the inside of hair. Examples of disulfide linkage reducing agent have been disclosed herein in detail.

As used herein, especially used in the softener part of the present invention, the term "alkalizer" generally refers to a substance capable of enabling the product prepared to achieve a certain acidity-alkalinity. For example, in one embodiment, the alkalizer in the softener part enables the pH of the softener part to be less than 8; or, for example, the alkalizer in the softener part enables the pH of the softener part to be less than 9; or, for example, the alkalizer in the softener part enables the pH of the softener part to be less than 10; or, for example, the alkalizer in the softener part enables the pH of the softener part to be less than 11. The pH can be determined directly by using a pH test paper, or determined by using a method well known in the art, for example, a pH-meter method. Optionally, the sample is pre-treated ad then is determined, for example, the sample is diluted suitably with water.

As used herein, the term "principal component" generally refers to active component used in the composition. For example, in the hair dyeing agent as recited in the first aspect, ferrous salt used as mortant active and gallic acid used as dye active are just active components that can be defined as "principal components". In relative to "principal component", other components in the composition are "auxiliary components", for example, antioxidant in the mordant of the present invention just can be called "auxiliary component".

With respect to the hair dyeing agent of the present invention and the softener part in the hair dyeing product combination of the present invention, they can be easily prepared by a person skilled in the art by referring to the relevant textbooks, for example, they can be prepared by the steps of mixing, heating, stirring, grinding, emulsifying, defining a volume, and sub-packaging etc. For another example, they can also be prepared by referring to the methods as taught in the Chapters relating to solutions, emulsions, pastes and the like in 《Pharmacy》 (Xi Nianzhu, Beijing, People's Health Publishing House, 1994). This document is incorporated herein by reference.

With respect to the hair dyeing product combination of the present invention, the softener therein can also be mixed uniformly, just before use, with the hair dyeing agent as recited in any item of the first aspect, and then the resulting mixture is applied onto the hair for dyeing. Thus, the two parts, i.e., the softener and the hair dyeing agent, in the present invention can be stored separately, so as to ensure their stability. Meanwhile, mixing uniformly the two parts just before use is also convenient for the use by the consumer.

The hair dyeing agent and the hair dyeing product combination comprising the hair dyeing agent in the present invention do not contain aromatic amine compounds such as thioglycolic acid, p-phenylenediamine and hydrogen peroxide, thus they are safe and not-stimulating, and have no possibility of latent carcinogenesis. The research results showed that, when the product was applied to people with white hairs, a allergenicity of 0% was obtained; after dyeing, the hair exhibited a natural black color and could be kept from discoloration for about 50 days. In addition, by adjusting the pH of the hair dyeing agent as recited in the first aspect within a suitable range, it is possible to ensure the stability of the product and the hair dyeing effect of the product within the shelf period, and moreover, the product can be used for multiple times after unsealed. Therefore, the dyed hair by using the hair dyeing agent of the present invention is good in dyeing chroma and fastness, natural and bright, and the use of the hair dyeing agent of present invention is characterized by simple operation, short dyeing time, no damage to skin and hair, good safety and reliability.

MODE OF CARRYING OUT THE INVENTION

The present invention is further illustrated by the following examples, comparative examples and test examples. However, it shall be understood that these examples, comparative examples and test examples are only used to specifically set forth the present invention, rather than being understood that they are used to limit the present invention in any form.

The present invention makes a general and/or specific description on the materials and methods used in the experiments. Although many materials and operation methods used for achieving the object of the present invention are well known in the art, the present invention still makes a description as detailed as possible herein. It is clear to a person skilled in the art that, hereinafter, if not especially indicated, the materials and operation methods used in the present invention are well known in the art.

Example 1

1) Softener part (formulated in a total amount of 100 g): 5 g N-acetylcysteine, 5 g sodium thiosulfates, 2 g sodium dodecyl sulfate, 3 g sodium lauryl ether sulfate, 0.6 g hydroxyethyl cellulose, 2 g propylene glycol, 0.2 g EDTA-2Na, arginine:monoethanolamine=1:1 (weight ratio) used to adjust pH=10.0 (test paper), the balance deionized water; the above components were mixed with stirring to make a gel.

2) Hair dyeing agent part (formulated in a total amount of 100 g): 8 g cetyl/stearyl alcohol, 6 g Ceteareth-6, 4 g sodium dodecyl sulfate, 5 g ferrous gluconate, 1.5 g cysteine hydrochloride, 2 g lanolin, 2 g white vaseline, 5 g methyl gallate, 4 g propylene glycol, 0.25 g methylparaben, 0.25 g propylparaben, monoethanolamine used to adjust pH=8.0 (test paper), the balance deionized water; the above components were mixed with stirring to make a paste.

3) Experiment of dyeing hair bundle: in use, without the necessity of washing hair, the softener part was directly applied onto the hair with a comb repeatedly till uniform, and then kept at a temperature of 25° C. for 30 minutes; after washing the hair, the hair dyeing part was applied uniformly onto the hair, and then kept at a temperature of 25° C. for 5 minutes. The hair was washed with warm water, and then air dried or blow dried.

The results showed that the hair bundle dyed with the hair dyeing agent of the present example was good in chroma and fastness; after being stored in an oven of 40° C. for two months, the sample was taken out and then stored in a refrigerator of 0° C., after two months, it was observed that the sample was good in appearance stability, and exhibited a dyeing effect consistent with that before the storage.

In the following Examples 2 to 4, only the formulas of the softener part and the hair dyeing agent part were listed, and the method of formulating them is similar to that used in Example 1.

Example 2

1) Softener part (formulated in a total amount of 100 g): 1.5 g cysteine, 0.5 g sodium bisulfites, 1 g sodium lauryl ether sulfate, 0.1 g hydroxypropylmethyl cellulose, 2 g propylene glycol, 0.2 g EDTA-2Na, diethanolamine used to adjust pH=11.0 (test paper), the balance deionized water.

2) Hair dyeing agent part (formulated in a total amount of 100 g): 8 g cetyl/stearyl alcohol, 7 g hydroxyethyl cellulose, 5 g Ceteareth-6, 5 g Ceteareth-25, 10 g sodium lauryl ether sulfate, 10 g cocamido propyl betaine, 15 g ferrous nitrate, 4 g acetylcysteine, 4 g cysteine hydrochloride, 2 g lanolin, 2 g white vaseline, 10 g propyl gallate, 4 g propylene glycol, 0.1 g hydantoin, monoethanolamine used to adjust pH=1.5 (test paper), the balance deionized water.

3) Experiment of dyeing hair bundle: in use, without the necessity of washing hair, the softener part was directly applied onto the hair with a comb repeatedly till uniform, and then kept at a temperature of 15° C. for 60 minutes; after washing the hair, the hair dyeing agent part was applied uniformly onto the hair, and then kept at a temperature of 15° C. for 20 minutes. The hair was washed with warm water, and then air dried or blow dried.

The results showed that the hair bundle dyed with the hair dyeing agent of the present example was good in chroma and fastness; after being stored in an oven of 40° C. for two months, the sample was taken out and then stored in a refrigerator of 0° C., after two months, it was observed that the sample was good in appearance stability, and exhibited a dyeing effect consistent with that before the storage.

Example 3

1) Softener part (formulated in a total amount of 100 g): 14 g N-acetylcysteine, 15 g cysteine, 1 g sodium sulfites, 5 g cocamido propyl betaine, 5 g sodium lauryl ether sulfate, 2 g xanthan gum, 2 g propylene glycol, 0.2 g EDTA-2Na, ammonia:monoethanolamine=1:1 (weight ratio) used to adjust pH=8.0 (test paper), the balance deionized water.

2) Hair dyeing agent part (formulated in a total amount of 100 g): 1 g hydroxypropylmethyl cellulose, 1 g Ceteareth-6, 1 g ferrous chloride, 0.1 g sodium ascorbate, 2 g lanolin, 2 g white vaseline, 0.5 g gallic acid, 4 g propylene glycol, 1.5 g phenoxyethanol, monoethanolamine used to adjust pH=2.5 (test paper), the balance deionized water.

3) Experiment of dyeing hair bundle: in use, without the necessity of washing hair, the softener part was directly applied onto the hair with a comb repeatedly till uniform, and then kept at a temperature of 60° C. for 5 minutes; after washing the hair, the hair dyeing agent part was applied uniformly onto the hair, and then kept at a temperature of 60° C. for 2 minutes. The hair was washed with warm water, and then air dried or blow dried.

The results showed that the hair bundle dyed with the hair dyeing agent of the present example was good in chroma and fastness; after being stored in an oven of 40° C. for two months, the sample was taken out and then stored in a refrigerator of 0° C., after two months, it was observed that the sample was good in appearance stability, and exhibited a dyeing effect consistent with that before the storage.

Example 4

1) Softener part (formulated in a total amount of 100 g): 15 g N-acetylcysteine, 0.5 g sodium sulfites, 3 g urea, 4 g sodium dodecyl sulfate, 5 g cocamido propyl betaine, 0.5 g carbomer, 2 g propylene glycol, 0.2 g EDTA-2Na, monoethanolamine used to adjust pH=9.5 (test paper), the balance deionized water; the above components were mixed with stirring to make a gel.

2) Hair dyeing agent part (formulated in a total amount of 100 g): 5 g cetyl/stearyl alcohol, 1 g Ceteareth-6, 1 g Ceteareth-25, 2 g oleyl alcohol, 1 g sodium dodecyl sulfate, 5 g ferrous sulfate, 3 g cysteine hydrochloride, 2 g lanolin, 2 g white vaseline, 1 g gallic acid, 4 g propylene glycol, 0.25 g methylparaben, 0.15 g propylparaben, monoethanolamine used to adjust pH=3.0 (test paper), the balance deionized water; the above components were mixed with stirring to make a paste.

3) Experiment of dyeing hair bundle: in use, without the necessity of washing hair, the softener part was directly applied onto the hair with a comb repeatedly till uniform, and then kept at a temperature of 30° C. for 30 minutes; after washing the hair, the hair dyeing component was applied uniformly onto the hair, and then kept at a temperature of 30° C. for 5 minutes. The hair was washed with warm water, and then air dried or blow dried.

The results showed that the hair bundle dyed with the hair dyeing agent of the present example was good in chroma and fastness; after being stored in an oven of 40° C. for two months, the sample was taken out and then stored in a refrigerator of 0° C., after two months, it was observed that the sample was good in appearance stability, and exhibited a dyeing effect consistent with that before the storage.

Example 5

1) Softener part (formulated in a total amount of 100 g): 8 g cysteine hydrochloride, 1.5 g sodium sulfites, 5 g cocamido propyl betaine, 0.8 g sodium carboxymethyl cellulose, 2 g propylene glycol, 0.2 g EDTA-2Na, ammonia used to adjust pH=9.0 (test paper), the balance deionized water; the above components were mixed with stirring to make a gel.

2) Hair dyeing agent part (formulated in a total amount of 100 g): 6 g carbomer, 2 g Ceteareth-6, 2 g Ceteareth-25, 10 g oleyl alcohol, 5 g ferrous lactate, 3 g acetylcysteine, 2 g sodium ascorbate, 2 g lanolin, 2 g white vaseline, 5 g propyl gallate, 4 g propylene glycol, 0.1 g methylparaben, 0.1 g propylparaben, 0.5 g phenoxyethanol, monoethanolamine used to adjust pH=4 (test paper), the balance deionized water; the above components were mixed with stirring to make a paste.

3) Experiment of dyeing hair bundle: in use, without the necessity of washing hair, the softener part was directly applied onto the hair with a comb repeatedly till uniform, and then kept at a temperature of 25° C. for 30 minutes; after washing the hair, the hair dyeing agent part was applied uniformly onto the hair, and then kept at a temperature of 25° C. for 5 minutes. The hair was washed with warm water, and then air dried or blow dried.

The results showed that the hair bundle dyed with the hair dyeing agent of the present example was good in chroma and fastness; after being stored in an oven of 40° C. for two months, the sample was taken out and then stored in a refrigerator of 0° C., after two months, it was observed that the sample was good in appearance stability, and exhibited a dyeing effect consistent with that before the storage.

Comparative Example 1

Sanjing Plant Hair Dyeing Agent

1) Three-part type: including 1# hair dyeing composition, 2# hair dyeing composition and 3# hair dyeing composition. 1# hair dyeing composition was liquid, 2# hair dyeing composition and 3# hair dyeing composition were powders.

2) Experiment of dyeing hair bundle: 1# hair dyeing composition was poured into a clean non-metal vessel, to which sorghum essence was then poured, followed by mixing uniformly. The resulting solution was applied onto the hair with a brush thoroughly and repeatedly till uniform, and then a cap was put on the hair, followed by keeping for 25~30 minutes (it was suggested that the temperature should be not lower than 20° C.). Thereafter, the hair was washed with warm water and dried. 2# hair dyeing composition (powder) was poured into a clean non-metal vessel, to which 50 ml clean water was added, followed by thoroughly mixing till uniform, and was applied onto the hair in a similar way to the application of 1# hair dyeing composition, and then kept for 10 minutes. Thereafter, the hair was washed with warm water and dried. 3# hair dyeing composition (powder) was used in a similar way to the operation of 2# hair dyeing composition, and then kept for 10 minutes. Thereafter, the hair was washed with warm water and dried.

Comparative Example 2

Yinpin Natural Hair Dyeing Agent

1) Three-part type: including 1# hair dyeing composition, 2# hair dyeing composition and 3# hair dyeing composition, all of them were liquid.

2) Experiment of dyeing hair bundle: hair was washed with shampoo and dried. 1# hair dyeing composition was applied onto the hair repeatedly till uniform, then a shower cap was put on the hair, and the shower cap was covered with a dry towel, followed by uniformly heating with a hair dryer at a temperature that is slightly higher than body temperature (not lower than 40° C.) for 20~30 minutes. Thereafter, the hair was washed with warm water and dried. 2# hair dyeing composition was applied onto the hair in a similar way to the application of 1# hair dyeing composition. Without the use of a shower cap and heating, after waiting for 15~20 minutes, the hair was washed with warm water and dried. 3# hair dyeing composition was used in a similar way to the application of 2# hair dyeing composition. After waiting for 10 minutes, the hair was washed with warm water and dried.

Comparative Example 3

Clove Hair Dyeing Agent

1) Two-part type: including 1# hair dyeing composition and 2# hair dyeing composition, both of them were liquid.

2) Experiment of dyeing hair bundle: hair was washed with shampoo and dried. 1# hair dyeing composition was applied onto the hair repeatedly till uniform, and then a shower cap was put on the hair, followed by heating with a steam generator for 25~30 minutes. Thereafter, the hair was washed with warm water and dried. 2# hair dyeing composition was applied onto the hair in a similar way to the application of 1# hair dyeing composition. Without the use of a shower cap, the hair was directly heated with a steam generator for 20 minutes. Thereafter, the hair was washed with warm water and dried.

Experimental Example

Experiment on Chroma and Fastness of Hair Bundle and Experiment on Stability of Formulations 1) Experimental Method Hair bundle: white hairs taken from the top of head of the same person with white hairs.

Chroma of hair bundle: the dyed hairs were detected by using a chroma meter, and simultaneously observed by naked eyes.

Fastness of hair bundle: the dyed hairs were radiated in sunlight to investigate their sunlight-resistant fastness; the dyed hairs were washed with market-sold shampoo to investigate their washing-resistant fastness.

Stability of formulation: after being stored in an oven of 40° C. for two months, the sample was taken out and then stored in a refrigerator of 0° C., after two months, the formulation sample was observed and used to hair dyeing experiment.

Repetitive use: after unsealed, the formulation sample was placed for 1 month, 2 months, 4 months and 6 months respectively, and then observed with regard to its state and subjected to hair dyeing experiment.

2) Experimental Results

The hairs were dyed according to the methods as described in Example 5, Comparative Example 1, Comparative Example 2 and Comparative Example 3 respectively, and the stability and repetitive use of the four formulations were investigated.

The results of dyeing the hair bundle by using the hair dyeing agent of Example 5 were as follows: the dyed hair bundle was black as detected by using a chroma meter, and the case is the same as observed by naked eyes. The experimental results of fastness showed that: after radiated in sunlight for 50 days and washed for 50 times, no discoloration was observed. Both the softener part and the hair dyeing agent part were subjected to stability experiments, and it was observed that the appearance thereof had no obvious change, and the dyeing results were consistent before and after investigation in the stability experiments. The experimental results of repetitive uses showed that: after placed for 1 month, 2 months, 4 months and 6 months when the formulations are unsealed, the softener part had no obvious change in appearance, and the hair dyeing agent part had no obvious change except that the portion at the open end in contact with air became discolored, while the dyeing results were consistent before and after the experiments.

The results of dyeing the hair bundle by using the hair dyeing agent of Comparative Example 1 were as follows: the hair bundle was dyed at 20° C. according to the instructions, and the colorizing effect was not ideal. The colorizing effect at 25° C. was relatively satisfactory. The dyed hair bundle was black as detected by using a chroma meter, and the case is the same as observed by naked eyes. The experimental results of fastness showed that: after radiated in sunlight for 50 days and washed for 50 times, no discoloration was observed. 1# hair dyeing composition, 2# hair dyeing composition and 3# hair dyeing composition were all subjected to stability experiments, and it was observed that 1# hair dyeing composition significantly became dilute in appearance after investigation in the stability experiments, and 2# hair dyeing composition and 3# hair dyeing composition had no obvious change in appearance, and the hair bundle as dyed therewith at 25° C. was purple. The experimental results of repetitive uses showed that: on the second day after unsealing, 1# hair dyeing composition became turbid and discolored, 2# hair dyeing composition (powder) and 3# hair dyeing composition became discolored, and the hair bundle as dyed therewith at 25° C. was pale purple.

The results of dyeing the hair bundle by using the hair dyeing agent of Comparative Example 2 were as follows: the dyed hair bundle was black as detected by using a chroma meter, and the case is the same as observed by naked eyes. The experimental results of fastness showed that: after radiated in sunlight for 50 days and washed for 50 times, no discoloration was observed. 1# hair dyeing composition, 2# hair dyeing composition and 3# hair dyeing composition were all subjected to stability experiments, and it was observed that the three compositions all significantly became dilute in appearance after investigation in the stability experiments, and the hair bundle as dyed therewith was purple. The experimental results of repetitive uses showed that: on the second day after unsealing, 1# hair dyeing composition, 2# hair dyeing composition and 3# hair dyeing composition became turbid and discolored, and the hair bundle as dyed therewith was pale purple.

The results of dyeing the hair bundle by using the hair dyeing agent of Comparative Example 3 were as follows: the dyed hair bundle was black as detected by using a chroma meter, and the case is the same as observed by naked eyes. The experimental results of fastness showed that: after radiated in sunlight for 50 days and washed for 50 times, no discoloration was observed. 1# hair dyeing composition and 2# hair dyeing composition were both subjected to stability experiments, and it was observed that the two compositions both significantly became dilute in appearance after investigation in the stability experiments, and the hair bundle as dyed therewith was purple. The experimental results of repetitive uses showed that: on the second day after opening, 1# hair dyeing composition and 2# hair dyeing composition became turbid and discolored, and the hair bundle as dyed therewith was pale purple.

The operating modes and repetitive use situations of the four formulations were listed in the following table.

| Test example | form | Times of washing | Times of applying | Treatment temperature | Treatment tool | Treatment time/min | Whether repetitive use is ok |
|---|---|---|---|---|---|---|---|
| Example 5 | Two-part | Two | Two | 25° C. | No need | 35 | Yes |
| Com. Example 1 | Three-part | Three | Three | 25° C. | No need | 50 | No |
| Com. Example 2 | Three-part | Four | Three | 40° C. | Hair dryer | 60 | No |

-continued

| Test example | form | Times of washing | Times of applying | Treatment temperature | Treatment tool | Treatment time/min | Whether repetitive use is ok |
|---|---|---|---|---|---|---|---|
| Com. Example 3 | Two-part | Three | Two | 50° C. | Steam generator | 50 | No |
| Example 5* | Two-part | One | One | 25° C. | No need | 30 | Yes |

Notes:
*indicated the results of uniformly pre-mixing the softener part and the hair dyeing agent part just before use and then hair dyeing. That is, before experiment, the softener part and the hair dyeing agent part according to Example 5 were uniformly mixed in a weight ratio of about 1:1; without the necessity of washing hair, the resulting mixture was directly applied onto the hair with a comb repeatedly till uniform, and then kept at a temperature of 25° C. for 30 minutes. The dyed hair was washed with warm water, and air dried or blow dried, and then the dyed hair were evaluated. The experimental results of hair bundle dyed in such manner were as follows: the dyed hair bundle was black as detected by using a chroma meter, and the case is the same as observed by naked eyes. The experimental results of fastness showed that: after radiated in sunlight for 50 days and washed for 50 times, no discoloration was observed. As could be seen from the results, the operation mode of uniformly pre-mixing the softener part and the hair dyeing agent part just before use and then hair dyeing reduces the times of washing and of applying.

In addition, the results of applying the hair dyeing agent of Example 5 in the present invention to people with white hairs showed that: the dyed hair exhibited a natural black color, and could be kept from discoloration for about 50 days, while the allergenicity was 0%.

The invention claimed is:

1. A hair dyeing agent, which comprises an effective amount of a dye active, an effective amount of a mordant active, a stabilizer and water, and optionally a carrier and/or an excipient.

2. The hair dyeing agent according to claim 1, wherein the dye active is one or more selected from gallic acid and salts or esters thereof; and/or the amount of the dye active, based on the total weight of the hair dyeing agent, is 0.5~10% (wt).

3. The hair dyeing agent according to claim 2, wherein the dye active is gallic acid.

4. The hair dyeing agent according to claim 1, wherein the mordant active is a ferrous salt; and/or the amount of the mordant active, based on the total weight of the hair dyeing agent, is 1~15% (wt).

5. The hair dyeing agent according to claim 4, wherein the ferrous salt is selected from ferrous sulfate, ferrous chloride, ferrous nitrate, ferrous gluconate, ferrous lactate, and ferrous fumarate.

6. The hair dyeing agent according to claim 1, wherein the stabilizer is selected from sulfites, bisulfites, thiosulfates, ascorbic acid or salts thereof, cysteine or derivatives and salts thereof; and/or the amount of the stabilizer, based on the total weight of the hair dyeing agent, is 0.1~8% (wt).

7. The hair dyeing agent according to claim 1, characterized in one or more of the following items i)-iv):
  i) which further comprises a penetration enhancer and/or a thickener;
  ii) the penetration enhancer includes chemical penetration enhancers including azone and homologues thereof, organic acids and esters thereof, organic solvents, and surfactants including anionic surfactants, nonionic surfactants, and amphoteric surfactants; Chinese medicine penetration enhancers including terpenes, essential oils, and lactone; and any combination of the foregoing;
  iii) the thickener is one or more selected from fatty alcohols or high molecular polymers; and
  iv) which has a pH value of 1.5~8.

8. A hair dyeing product combination which comprises two parts, a softener part and the hair dyeing agent part according to any of claims 1 to 7.

9. The hair dyeing product combination according to claim 8, wherein the softener comprises an effective amount of a disulfide linkage reducing agent, an alkalizer, and water.

10. The hair dyeing product combination according to claim 9, wherein the disulfide linkage reducing agent in the softener is one or more selected from mercapto compounds, urea, thiosulfates, sulfites, and bisulfites.

11. The hair dyeing product combination according to claim 10, wherein the disulfide linkage reducing agent in the softener is cysteine or derivatives and salts thereof.

12. The hair dyeing product combination according to claim 8, wherein the alkalizer in the softener is one or more selected from ornithine, arginine, lysine, ammonia, ethanolamines, alkyl alcohol amide, hydroxides, or carbonate-containing compositions.

13. The hair dyeing product combination according claim 8, which further comprises information about a method of using the hair dyeing product combination; the information at least comprises the following:
  a) applying the softener onto the hair; and
  b) applying the hair dyeing agent onto the hair.

14. The hair dyeing product combination according to claim 8, which further comprises information about a method of using the hair dyeing product combination; the information at least comprises the following:
  i) uniformly mixing the softener and the hair dyeing agent in a weight ratio of 1:0.1 to 1:10; and
  ii) applying the mixture obtained in the above i) onto the hair.

15. A method of using the hair dyeing product combination according to claim 8, which comprises the steps of:
  a) applying the softener onto the hair; and
  b) applying the hair dyeing agent onto the hair.

16. A method of using the hair dyeing product combination according to claim 8, which comprises the steps of:
  i) uniformly mixing the softener and the hair dyeing agent in a weight ratio of 1:0.1 to 1:10; and
  ii) applying the mixture obtained in the above i) onto the hair.

* * * * *